(12) United States Patent
Malmendier

(10) Patent No.: US 11,700,872 B2
(45) Date of Patent: Jul. 18, 2023

(54) LIQUID COMPOSITION COMPRISING PHYCOCYANIN

(71) Applicant: B BLUE NUTRACEUTICALS, Verviers (BE)

(72) Inventor: Olivier Malmendier, Verviers (BE)

(73) Assignee: B BLUE NUTRACEUTICALS, Verviers (BE)

( * ) Notice: Subject to any disclaimer, the term of this patent is extended or adjusted under 35 U.S.C. 154(b) by 254 days.

(21) Appl. No.: 17/019,138

(22) Filed: Sep. 11, 2020

(65) Prior Publication Data
US 2022/0079199 A1   Mar. 17, 2022

(51) Int. Cl.
| | |
|---|---|
| A23L 2/38 | (2021.01) |
| A23L 33/105 | (2016.01) |
| A61K 47/10 | (2017.01) |
| A61K 47/26 | (2006.01) |
| A61K 47/42 | (2017.01) |
| A61K 35/748 | (2015.01) |
| A61K 47/02 | (2006.01) |
| A61K 47/12 | (2006.01) |
| A61K 31/07 | (2006.01) |
| A61K 31/375 | (2006.01) |
| A61K 31/355 | (2006.01) |
| A23L 2/44 | (2006.01) |
| A23L 2/56 | (2006.01) |
| A23L 2/60 | (2006.01) |
| A23L 2/68 | (2006.01) |
| A23L 33/155 | (2016.01) |
| A23L 33/15 | (2016.01) |
| A23L 2/74 | (2006.01) |
| A23L 2/54 | (2006.01) |
| A23L 2/46 | (2006.01) |
| B65B 3/04 | (2006.01) |
| A61K 38/16 | (2006.01) |

(52) U.S. Cl.
CPC ............. *A23L 33/105* (2016.08); *A23L 2/44* (2013.01); *A23L 2/46* (2013.01); *A23L 2/54* (2013.01); *A23L 2/56* (2013.01); *A23L 2/60* (2013.01); *A23L 2/68* (2013.01); *A23L 2/74* (2013.01); *A23L 33/15* (2016.08); *A23L 33/155* (2016.08); *A61K 31/07* (2013.01); *A61K 31/355* (2013.01); *A61K 31/375* (2013.01); *A61K 35/748* (2013.01); *A61K 38/168* (2013.01); *A61K 47/02* (2013.01); *A61K 47/10* (2013.01); *A61K 47/12* (2013.01); *A61K 47/26* (2013.01); *A61K 47/42* (2013.01); *B65B 3/04* (2013.01); *A23V 2002/00* (2013.01)

(58) Field of Classification Search
CPC ....................................................... A23L 2/38
See application file for complete search history.

(56) References Cited

FOREIGN PATENT DOCUMENTS

| | | |
|---|---|---|
| CN | 103054117 A | 4/2013 |
| JP | 2005295829 | 10/2005 |
| RU | 2283003 C1 | 9/2006 |
| WO | WO-2018229365 A1 * | 12/2018 ............. A23L 17/60 |

OTHER PUBLICATIONS

Weikle, "Determination of citric acids in fruit juices using HPLC," Concordia College Journal of Analytical Chemistry 3:57-62, 2012.*

* cited by examiner

*Primary Examiner* — Rosanne Kosson
(74) *Attorney, Agent, or Firm* — Ferguson Case Orr Paterson

(57) ABSTRACT

A beverage comprising water, phycocyanin and having a heavy metals content below a threshold amount, the beverage having a pH within a certain range and a minimum acceptable shelf life, by optimizing the steps in the production of the beverage, but without adding many chemical substances and without carrying out harsh chemical treatment on the natural substances. By the combined use of a phycocyanin obtained, for example, by ultrafiltration or by treatment under pressure, with sterile demineralized water, and mixing the other components separately from the bacteria and other contaminants, in an aseptic environment, it is possible to provide a beverage that has nutraceutical effects, with low heavy metals content, at a suitable pH, and with an extended shelf life.

25 Claims, No Drawings

LIQUID COMPOSITION COMPRISING PHYCOCYANIN

BACKGROUND OF THE DISCLOSURE

Field of the Disclosure

The present disclosure relates to the general field of the manufacture of liquid compositions, and more specifically the manufacture of edible liquid compositions comprising phycocyanin.

Description of the Related Art

For some years consumers have displayed increasing interest in dietary compositions supplying nutrients that are beneficial to health.

Accordingly, algae and the compounds that can be extracted from them have highly valued qualities. A great many studies in fact mention their anti-cancer, anti-ageing or anti-cholesterol properties.

Among the compounds of choice that can be extracted from algae (such as *Spirulina*), phycocyanin has a combination of excellent properties: functional food, naturally fluorescent molecule, and powerful dye.

The benefits of phycocyanin and its nutraceutical effect are well known from scientific literature. In fact, among the numerous health benefits of phycocyanin are, for example, its antioxidant activity, inhibition of lipid peroxidation, anti-inflammatory properties, stimulation of the immune defenses (it promotes the production of stem cells, white and red blood cells, antibodies and platelets), oxygenation of the blood, recycling of lactates, participation in protection and detoxification of the liver or else its inhibitory activity on the growth of cancer cells and its anti-allergic activity.

Furthermore, phycocyanin is also able to prevent the development of certain diseases in which oxidative stress is involved, and therefore the effects of ageing.

It is well understood that the use of phycocyanin for its nutraceutical effect in liquid compositions is particularly sought-after by consumers.

However, the use of this molecule, which is sensitive to heat, light and bacteriological contaminants, is subject to considerable constraints, both at the level of chemical formulation and at the level of the method of manufacture to be employed.

It is in fact known that phycocyanin must be extracted and manipulated in sterile conditions, that its maximum stable temperature is about 45° C. whereas its thermal denaturation temperature is about 60° C., and that it has maximum stability when the pH of the medium is between 5 and 7, with any substantial variation beyond these limits leading to precipitation of the molecules.

It is thus necessary to find a balance between all these requirements in order to preserve its advantageous properties.

Thus, although it seems relatively easy to formulate water-based beverages or syrups, as described for example in the documents CN103054117 A, JP2005295829 A2, or RU2283003 C1, beverage manufacture is still a significant challenge.

In this context, it is desirable to obtain beverages that are more natural, containing the least possible amount of chemical additives, and this is made even more complex by the demand for a product of biological origin.

In general, the use of natural extracts that have undergone little or no chemical treatment means that bacteria are present, and this reduces shelf life considerably.

Moreover, "natural origin" implies a desire to avoid chemical substances or substances that are harmful to health. In the case of natural substances, however, it is necessary to avoid the presence of contaminants from the environment from which the natural substance has been obtained.

Generally, as it is not desirable to perform chemical extraction of these contaminants, there is a tendency to reduce the content of contaminants by diluting the natural substance, to the detriment of the nutraceutical effect, which is not desired by consumers, who require the nutraceutical effect of the natural substance. It is also necessary to reduce the bacterial content of these natural substances.

More particularly in the case of carbonated beverages, this necessarily comprises a step of carbonation of the beverage, which leads to the formation of products in a pH range generally not exceeding a value of 4 (this acidity being due at least partially to the reaction of carbon dioxide with water, leading to the formation of carbonic acid). For example, colas have a pH below 3.3, whereas lemonades do not exceed a pH of 3.8. This pH range is prohibitive for the use of phycocyanin.

There is therefore a real need to supply a product comprising a natural extract that is sensitive to light and heat, which in order to be usable industrially in a cost-effective manner while having a nutraceutical effect, must have an extended shelf life, without having molecules that are controversial for health, or bacteria beyond the threshold considered unsuitable for consumption.

DETAILED DESCRIPTION OF THE DISCLOSURE

It was possible, according to embodiments of the present disclosure, to supply a beverage that has nutraceutical effects, with a low heavy metals content and an extended shelf life.

In fact, one embodiment of the present disclosure provides a beverage comprising water, phycocyanin at a content of at least 1.5% w/v of said beverage and having a heavy metals content below 1 ppm, said beverage having a pH between 4.0 and 5.5 and a shelf life of at least 6 months, by optimizing the steps in the production of the beverage, but without adding many chemical substances and without carrying out harsh chemical treatment on the natural substances.

In fact, by the combined use of a phycocyanin obtained for example by ultrafiltration or by treatment under pressure, with sterile demineralized water plus mixing the other components separately from the bacteria and other contaminants, in an aseptic environment, it was possible to supply a beverage that has nutraceutical effects, with low heavy metals content, at a suitable pH and with an extended shelf life.

Said beverage is remarkable in that it has a pH between 4.0 and 5.5.

Advantageously, the beverage according to an embodiment of the present disclosure comprises phycocyanin at a content of at least 1.8%, preferably of at least 2.0%, preferably of at least 2.2% and even more preferably of at least 2.4% w/v of said beverage.

In fact, because it has a phycocyanin content at this level, the beverage according to an embodiment of the present disclosure possesses nutraceutical activity and highly desirable qualities.

Particularly advantageously, the beverage according to an embodiment of the present disclosure has a shelf life of at least 8 months, preferably of at least 10, even more advantageously of at least 12 months.

It seemed particularly surprising that the beverage according to an embodiment of the present disclosure makes it possible to supply a phycocyanin content that is advantageous for the nutraceutical effect while having a heavy metals content below 1 ppm and having a shelf life that is particularly advantageous for the consumer and for the manufacturers. This is all the more surprising taking into account the sensitivity of phycocyanin and high constraints for formulation as a liquid composition having a nutraceutical effect.

Advantageously, an embodiment of the present disclosure comprises at least one pH adjuster, preferably of natural origin.

Preferably, an embodiment of the present disclosure comprises at least one preservative, preferably of natural origin.

The terms "pH adjuster of natural origin" and "preservative of natural origin" mean, in the sense of the present disclosure, that these compounds are non-chemical, and are free from substances derived from petrochemistry.

Preferably, said pH adjuster is a basifying agent, i.e., an agent capable of increasing the pH of the composition when it is added.

Advantageously, said at least one preservative is selected from the group comprising: sodium benzoate, potassium sorbate, benzoic acid, sorbic acid, calcium sorbate, sodium ascorbate, citric acid, sodium benzoate, edetates, a paraben such as methyl, ethyl, propyl and butyl p-hydroxybenzoates, domiphen bromide, sodium propionate, propylene glycol, alcohols, tartaric acid, lactic acid, carbon dioxide, acetic acid and mixtures thereof.

Advantageously, said at least one pH adjuster is selected from the group comprising: lactic acid, acetic acid, tartaric acid, citric acid, carbonic acid, and mixtures thereof.

In one suitable embodiment according to the present disclosure, said at least one pH adjuster is a mixture of 2, 3, 4 or 5 acids selected from lactic acid, acetic acid, tartaric acid, citric acid, carbon dioxide.

Any combination of conventional pH adjusters and/or preservatives may of course be considered, and a person skilled in the art is able to select the most suitable combination as a function of the characteristics desired for said beverage.

According to another embodiment of the present disclosure, the beverage comprises a mixture of agents that are simultaneously pH adjusters and preservatives, in the form of a mixture of potassium sorbate and sodium benzoate.

In one suitable embodiment the final concentration of sodium benzoate, used alone in said carbonated beverage, does not exceed 0.3 grams per litre.

In another suitable embodiment the final concentration of sodium benzoate in said carbonated beverage is between 0.1 and 0.2 grams per litre.

In another suitable embodiment the final concentration of sodium benzoate in said carbonated beverage is 0.15 grams per litre.

In another suitable embodiment, when sodium benzoate is used in combination with potassium sorbate, the final concentration of sodium benzoate in said carbonated beverage is at most 0.15 grams per litre.

In yet another suitable embodiment, when sodium benzoate is used in combination with potassium sorbate, the final concentration of sodium benzoate in said carbonated beverage is 0.15 grams per litre.

In one suitable embodiment, the final concentration of potassium sorbate, used alone in said carbonated beverage, does not exceed 0.3 grams per litre.

In another suitable embodiment, the final concentration of potassium sorbate in said carbonated beverage is between 0.2 and 0.3 grams per litre.

In yet another suitable embodiment, the final concentration of potassium sorbate in said carbonated beverage is 0.25 grams per litre. In another embodiment, when potassium sorbate is used in combination with sodium benzoate, the final concentration of sodium benzoate in said carbonated beverage is at most 0.25 grams per litre.

In yet another suitable embodiment, when potassium sorbate is used in combination with sodium benzoate, the final concentration of sodium benzoate in said carbonated beverage is 0.25 grams per litre.

In one suitable embodiment according to the present disclosure, said at least one pH adjuster is also the preservative.

In one embodiment, said beverage comprises at least one flavouring. The flavouring may be in solid or liquid form.

In one embodiment, said flavouring is in liquid form. Said flavouring in liquid form may be alcoholized (i.e., its constituents are dissolved in a solvent comprising alcohol before it is added to the beverage according to the disclosure) or non-alcoholized (i.e., its constituents are dissolved in a solvent not comprising alcohol before it is added to the beverage according to the disclosure).

The flavouring may comprise at least one component among: gustatory agent, alcohol, stabilizer, antioxidant, preservative. The flavouring may comprise at least one gustatory agent able to impart a pleasant taste to the beverage.

In one embodiment, said flavouring is an alcoholized flavouring.

In this embodiment, the beverage, which may be carbonated, contains an alcohol concentration not exceeding 0.5% and/or has a degree of alcohol not exceeding 0.5 degree. In another embodiment, the carbonated beverage has a degree of alcohol not exceeding 0.36 degree. And in another embodiment, the carbonated beverage has a degree of alcohol not exceeding 0.15 degree (which corresponds to an alcohol concentration not exceeding 0.15%).

In one suitable embodiment, before it is added to the beverage according to the disclosure, the flavouring (of whatever nature) contains less than 5 wt % of pectin.

In another suitable embodiment, before it is added to the beverage according to the disclosure, the flavouring (of whatever nature) contains less than 5 wt % of a source of pectin.

In yet another suitable embodiment, before it is added to the beverage according to the disclosure, the flavouring (of whatever nature) does not contain pectin.

This signifies that it does not contain pectin and/or that it does not contain any possible source of pectin.

In one embodiment, said flavouring comprises at least one stabilizer from the group comprising: glucose, fructose, glycerine, glycerol and derivatives thereof, and mixtures thereof.

In another embodiment, said flavouring comprises a mixture of stabilizers consisting of a mixture of glucose and fructose.

Such a mixture may be derived from a natural source such as honey, or an artificial source, for example.

In one suitable embodiment, said flavouring comprises a mixture of stabilizers in the form of invert sugar (equimolar mixture of glucose and fructose).

In some embodiments, according to more developed variants of compositions, the flavouring may comprise at least one antioxidant, such as hydroxytyrosol.

Also, in some embodiments, according to more developed variants of compositions, the flavouring may comprise at least one agent for preserving its qualities, such as potassium sorbate or sodium ascorbate.

In some embodiments, the gustatory agent is also an alcohol and/or a stabilizer and/or an antioxidant and/or a preservative.

In some embodiments, said carbonated beverage according to the disclosure comprises at least one sweetener. Said sweetener may be natural or artificial. Said sweetener may be a sugar or any agent imparting a sweet flavour to said carbonated beverage, such as for example the polyols.

In one embodiment, said sweetener is selected from the group comprising: glucose, fructose, sucrose, lactose, maltose, agave, syrups thereof, and mixtures thereof.

In one suitable embodiment, said sweetener is fructose syrup.

In another suitable embodiment, the final concentration of fructose syrup in said beverage, in some cases carbonated, is between 10 and 70 grams per litre, said syrup being a syrup at 70 degrees.

In another suitable embodiment, the final concentration of fructose syrup in said carbonated beverage is between 30 and 60 grams per litre.

In another suitable embodiment, the final concentration of fructose syrup in said carbonated beverage is between 35 and 55 grams per litre.

In yet another suitable embodiment, the final concentration of fructose syrup in said carbonated beverage is 53.6 grams per litre.

In yet another suitable embodiment, said sweetener is agave syrup.

In one embodiment, said beverage contains less than 0.1 wt % of pectin.

In one embodiment, said beverage contains less than 0.1 wt % of a source of pectin.

In another embodiment, said beverage does not contain pectin.

This means that it does not contain pectin and/or that it does not contain any possible source of pectin.

In another embodiment of the present disclosure, the beverage further comprises a predetermined content of cytoplasmic component from *Spirulina* of at least 0.5%, in another embodiment of at least 0.75%, and in another embodiment of at least 1%.

Embodiments of the present disclosure may have pH ranges according to the following: between 4.1 and 5.4, between 4.2 and 5.3, between 4.2 and 5.2, between 4.3 and 5.1, between 4.3 and 5.0, between 4.3 and 4.9, between 4.4 and 4.8, between 4.4 and 4.7, and between 4.5 and 4.7.

In another suitable embodiment, said beverage, preferably carbonated, has a pH of 4.6±0.1.

The phycocyanin present in said beverage may be natural or artificial (i.e., synthesized in the laboratory).

The phycocyanin present in the beverage according to the disclosure is derived from a natural aqueous extract. The pH range defined above (4.0-5.5) is suitable for manufacturing a beverage according to the disclosure, as it is a compromise between the usual pH range of sodas (pH below 4) and the pH range most suitable for phycocyanin (pH between 5 and 7).

The phycocyanin may be obtained from at least one variety of algae that may belong to various phyla.

Some examples are: the Cyanophyta phylum (and more specifically the cyanobacteria including *Spirulina*), the Rhodophyta phylum (red algae) or the Cryptophyta phylum.

In other embodiments, the phycocyanin is obtained from *Spirulina* (*Spirulina platensis, Spirulina maxima, Arthrospira platensis*).

In one particular embodiment, the phycocyanin is obtained from *Spirulina platensis*.

In one embodiment of the present disclosure, said beverage further comprises at least one vitamin, more particularly an antioxidant vitamin, for example vitamin A, vitamin C, vitamin E.

One embodiment comprises a content of 2 mg of vitamin E per 100 mL of beverage according to the disclosure.

In another preferred embodiment, the beverage according to the present disclosure comprises a phycocyanin content above 2 mg per 100 mL of beverage, in another embodiment, above 3 mg per 100 mL of beverage, and in another embodiment, above 3.5 mg per 100 mL of beverage.

The beverage according to the embodiments of the disclosure is carbonated by adding at least one gas, dissolved in solution.

Advantageously, it is thus possible to use a single gas, a mixture of gases (injected together or separately), or different gases.

Advantageously, addition of the gas or gases may be carried out at one and the same time point or at different time points. The gas or gases may, for example, be selected from the group comprising: nitrogen, nitrogen dioxide, carbon dioxide.

In on embodiment, the dissolved gas is carbon dioxide in the form of bicarbonates $HCO_3^-$. However, it is possible to use a gas comprising nitrogen (the use of nitrogen dioxide being known for example in the preparation and drawing of certain beers).

In one suitable embodiment, the carbonated beverage according to the present disclosure has a content of bicarbonates $HCO_3^-$ between 2000 and 8000 mg/L, preferably between 2000 and 6000 mg/L, and in another embodiment, between 2000 and 4000 mg/L of carbonated beverage.

In a first exemplary embodiment, the beverage according to the present disclosure comprises carbonated water, 2% of phycocyanin, 4% of sweetener such as fructose syrup, 0.08% of natural flavouring, 2% of antioxidant such as vitamin E, 0.1% of potassium sorbate, 0.06% of sodium benzoate, by weight per volume of the beverage.

The beverage according to the first exemplary embodiment has a pH of 4.6, a heavy metals content below 1 ppm and a shelf life of at least 12 months.

In a second exemplary embodiment, the beverage according to the present disclosure comprises water, 2.4% of phycocyanin, 0.1% of concentrated lemon juice, 0.045% of natural flavouring, 2% of antioxidant such as vitamin E, 0.075% of potassium sorbate, 0.045% of sodium benzoate, by weight per volume of the beverage.

The beverage according to the second exemplary embodiment has a pH of 4.6, a heavy metals content below 1 ppm and a shelf life of at least 12 months.

In a third exemplary embodiment, the beverage according to the present disclosure comprises water, 2.4% of phycocyanin, 4.5% of sweetener such as agave syrup, 0.1% of concentrated lemon juice, 0.045% of natural flavouring, 2% of antioxidant such as vitamin E, 0.075% of potassium sorbate, 0.045% of sodium benzoate, by weight per volume of the beverage.

The beverage according to the third exemplary embodiment has a pH of 4.6, a heavy metals content below 1 ppm and a shelf life of at least 12 months.

In a fourth exemplary embodiment, the beverage according to the present disclosure comprises carbonated water, 2% of phycocyanin, 4% of sweetener such as fructose syrup, 0.08% of natural flavouring, 2% of antioxidant such as vitamin E, by weight per volume of the beverage.

The beverage according to the fourth exemplary embodiment has a pH of 4.6, a heavy metals content below 1 ppm and a shelf life of at least 12 months.

In a fifth exemplary embodiment, the beverage according to the present disclosure comprises water, 2.4% of phycocyanin, 0.1% of concentrated lemon juice, 0.045% of natural flavouring, 2% of antioxidant such as vitamin E, by weight per volume of the beverage.

The beverage according to the fifth exemplary embodiment has a pH of 4.6, a heavy metals content below 1 ppm and a shelf life of at least 12 months.

In a sixth exemplary embodiment, the beverage according to the present disclosure comprises water, 2.4% of phycocyanin, 4.5% of sweetener such as agave syrup, 0.1% of concentrated lemon juice, 0.045% of natural flavouring, 2% of antioxidant such as vitamin E, by weight per volume of the beverage.

The beverage according to the exemplary sixth embodiment has a pH of 4.6, a heavy metals content below 1 ppm and a shelf life of at least 12 months.

It is even more surprising that the formulation of beverages according to the present disclosure in a still water version, without carbonated water, is made possible, comprising a phycocyanin content of at least 1.5% w/v of beverage and having a shelf life of at least 6 months and preferably at least 12 months. Especially as phycocyanin is extremely sensitive, its formulation is complicated.

Furthermore, it surprising that the formulation of beverages according to the present disclosure in a preservative-free version is also made possible, comprising a phycocyanin content of at least 1.5% w/v of beverage and having a shelf life of at least 6 months and preferably at least 12 months. Especially as phycocyanin is extremely sensitive, its formulation is complicated and it is well known that the presence of a preservative stabilizes beverages over time, which is made possible according to the present disclosure without adding preservatives.

In order to facilitate methods of manufacture of said beverage, preferably carbonated, the present disclosure also relates to a concentrated composition, remarkable in that it comprises on the one hand one or more of the components of said beverage according to the disclosure, with the exception of water and phycocyanin, at a concentration multiplied by a factor n relative to their concentration in the beverage according to the disclosure, and on the other hand water at a concentration divided by said factor n.

Said concentrated composition makes it possible to prepare said beverage by means of a step of dilution in water.

Thus, one method of manufacturing a beverage according to the disclosure is remarkable in that it comprises the steps of:
  preparing a first mixture by adding, to sterile demineralized water, at least one compound selected from the group of pH adjusters, preservatives, sweeteners, flavourings, to give a pH between 4.0 and 5.5;
  debacterization treatment of the first mixture;
  preparing a second mixture comprising debacterized phycocyanin;
  preparing a third mixture formed from said debacterized first mixture and said debacterized second mixture in aseptic conditions so as to obtain a proportion of phycocyanin of at least 1.5% w/v of homogeneous beverage, optionally after dilution; and
  packaging said beverage in aseptic containers.

Preferably, said dilution is carried out before, during or after said third mixing, said dilution being carried out by adding water to said first mixture or to said second mixture or to said third mixture.

In one suitable embodiment, said second mixture is debacterized by a step of ultrafiltration or sterilization under pressure. Debacterization means any operation with the aim of eliminating bacteria, optionally said debacterization is a heat-controlled debacterization.

In one embodiment, said debacterization step is a pasteurization step carried out at a temperature between 60° C. and 100° C. or a step of high-pressure debacterization.

Heat-controlled debacterization means any operation with the aim of eliminating any bacteria present in solution by raising the temperature, such as pasteurization (temperatures from 60° C. to 100° C.)

In another embodiment, the method according to the present disclosure comprises a step of injecting carbon dioxide into said first mixture or said third mixture, at a predetermined pressure.

In one embodiment, gas injection is carried out at a pressure between 3 and 7 bar.

In another embodiment, gas injection is carried out at a pressure of 5 bar.

In another embodiment, the gas injected is carbon dioxide.

In another embodiment, the concentration of gas in the finalized beverage is between 2000 and 8000 mg/L, preferably between 2000 and 6000 mg/L, more preferably between 2000 and 4000 mg/L of carbonated beverage according to the disclosure.

In one embodiment, the step of debacterization of said first mixture is carried out under pressure, optionally at a pressure similar to that of carbon dioxide injection.

In one embodiment, the step of preparing said third mixture is carried out under pressure, optionally at a pressure similar to that of carbon dioxide injection.

In another embodiment, said second mixture further comprises cytoplasmic components from *Spirulina* of at least 0.5%, preferably of at least 0.75%, more particularly of at least 1% or more.

In one embodiment, injection of the second mixture comprising phycocyanin takes place under sterile conditions, using a sterile connection system.

In another embodiment, said sterile connection system comprises a filter having pores whose size is at most 0.5 microns.

In yet another embodiment, said filter has pores with a size of 0.2 microns.

In one embodiment, said sterile connection system provides connection between a first sterile tank containing said algal composition and a rotary valve piston pump.

In one embodiment, said piston pump is a sterilizable pump.

In another embodiment, said piston pump can be steam-sterilized.

Said pump provides injection of the algal composition and mixing thereof with the other components of the beverage, the whole being sent to a second sterile tank intended to contain the finished product.

Finally, it is noted that a person skilled in the art is able to select the components, the concentrations and the pressures that are the most suitable for the formulation and manufacture of said carbonated beverage and of said concentrated composition, as a function of the required final characteristics.

In one embodiment, said container is selected from the group comprising flasks, bottles, cans, pockets, cartons, or any other suitable container for containing said beverage, said container being made of glass, PET, biodegradable polymer.

Finally, it is noted that the present disclosure is not limited to just the embodiments described; it encompasses all embodiment and application variants based on the same principle.

I claim:

1. A beverage comprising:
   (a) water,
   (b) phycocyanin at a content of at least 1.5% w/v of said beverage and having a heavy metals content below 1 ppm, said beverage having a pH between 4.0 and 5.5, and
   (c) a pH adjuster and/or preservative, wherein said pH adjuster and/or preservative imparts a shelf life of at least 6 months to the beverage.

2. The beverage according to claim 1, further comprising at least one flavoring.

3. The beverage according to claim 2, characterized in that said flavoring comprises at least one stabilizer selected from the group consisting of glucose, fructose, glycerin, glycerol and derivatives thereof, and mixtures thereof.

4. The beverage according to claim 1, characterized in that it further comprises at least one sweetener selected from the group consisting of glucose, fructose, sucrose, lactose, maltose, agave, syrups thereof, and mixtures thereof.

5. The beverage according to claim 1, characterized in that it contains less than 0.1 wt % of pectin.

6. The beverage according to claim 1, wherein the phycocyanin is present in a preparation of *Spirulina*, and wherein the cytoplasmic component of the *Spirulina* in the beverage has a concentration of at least 0.5%.

7. The beverage according to claim 1, characterized in that the pH is in one of the pH ranges selected from the group consisting of between 4.1 and 5.4, between 4.2 and 5.3, between 4.2 and 5.2, between 4.3 and 5.1, between 4.3 and 5.0, between 4.3 and 4.9, between 4.4 and 4.8, between 4.4 and 4.7, and between 4.5 and 4.7.

8. The beverage according to claim 1, characterized in that the preservative is selected from the group consisting of: sodium benzoate, potassium sorbate, benzoic acid, sorbic acid, calcium sorbate, sodium ascorbate, citric acid, sodium benzoate, the edetates (EDTA or a salt thereof), methyl, ethyl, propyl and butyl p-hydroxybenzoates, domiphen bromide, sodium propionate, propylene glycol, alcohols, tartaric acid, lactic acid, carbon dioxide, acetic acid and mixtures thereof.

9. The beverage according to claim 1, wherein said pH adjuster is selected from the group consisting of lactic acid, acetic acid, tartaric acid, citric acid, carbonic acid, and mixtures thereof.

10. The beverage according to claim 7, wherein the pH adjuster is a mixture of 2, 3, 4 or 5 acids selected from the group consisting of lactic acid, acetic acid, tartaric acid, citric acid, and carbon dioxide.

11. The beverage according to claim 1, wherein said at least one pH adjuster is also the preservative.

12. The beverage according to claim 1, further comprising at least one vitamin selected from the group consisting of vitamin A, vitamin C, and vitamin E.

13. The beverage according to claim 1, wherein the phycocyanin content is from 2 mg to 3.5 mg per 100 mL of beverage.

14. The beverage according to claim 1, wherein the beverage is a carbonated beverage having a content of bicarbonates ($HCO_3^-$) between 2000 and 4000 mg/L.

15. A method for preparing the beverage of claim 1, comprising the steps of:
   (a) preparing a first mixture by adding, to sterile demineralized water, at least one compound that is a pH adjustor and/or a preservative, to give a pH between 4.0 and 5.5, optionally wherein a sweetener or flavoring is added to the first mixture;
   (b) sterilizing the first mixture;
   (c) preparing a second mixture comprising sterilized phycocyanin;
   (d) preparing a third mixture formed from said sterilized first mixture and said sterilized second mixture in aseptic conditions so as to obtain a proportion of phycocyanin of at least 1.5% w/v in the third mixture, wherein the third mixture is a homogeneous beverage; and
   (e) packaging said beverage in aseptic containers.

16. The method of claim 15, wherein said beverage is diluted, wherein said dilution is carried out before, during or after said third mixing, said dilution being carried out by adding water to said first mixture or said second mixture or said third mixture.

17. The method of claim 15, wherein said second mixture is sterilized by a step of ultrafiltration or of sterilization under pressure.

18. The method of claim 15, wherein said second mixture further comprises cytoplasmic components from *Spirulina* at a concentration of at least 0.5%.

19. The method of claim 15, wherein said sterilization step is a pasteurization step carried out at a temperature between 60° C. and 100° C. or a step of high-pressure sterilization.

20. The method of claim 15, characterized in that it comprises a step of injecting carbon dioxide into said first mixture or said third mixture, at a predetermined pressure.

21. The method of claim 20, wherein the step of sterilization of said first mixture is carried out under pressure, optionally at a pressure at or near that of the carbon dioxide injection.

22. The method of claim 15, wherein the step of preparing said third mixture is carried out under pressure, optionally at a pressure at or near that of the carbon dioxide injection.

23. The method of claim 15, wherein said container is selected from the group consisting of flasks, bottles, cans, pockets, and cartons, optionally wherein said container is made of glass, polyethylene terephthalate (PET), or a biodegradable polymer.

24. A beverage comprising:
   (a) water;
   (b) phycocyanin at a content of at least 1.5% w/v of said beverage;
   (c) heavy metals in an amount less than 1 ppm;
   (d) at least one pH adjuster;
   (e) at least one preservative; and
   (f) at least one flavoring; wherein said beverage has a pH between 4.0 and 5.5 and a shelf life of at least 6 months.

25. The beverage according to claim 1, wherein said at least one pH adjuster is carbonic acid.

\* \* \* \* \*